United States Patent
Matsuda et al.

(10) Patent No.: US 6,903,067 B2
(45) Date of Patent: Jun. 7, 2005

(54) FRAGRANCE COMPOSITION CONTAINING 3-(3-HEXENYL)-2-CYCLOPENTENONE

(75) Inventors: Hiroyuki Matsuda, Kanagawa (JP); Kenji Maruyama, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 147 days.

(21) Appl. No.: 10/309,096

(22) Filed: Dec. 4, 2002

(65) Prior Publication Data

US 2003/0158080 A1 Aug. 21, 2003

(30) Foreign Application Priority Data

Dec. 18, 2001 (JP) ........................................ 2001-385182
Dec. 18, 2001 (JP) ........................................ 2001-385183

(51) Int. Cl.$^7$ .............................................. A61K 7/46
(52) U.S. Cl. .............................. 512/27; 512/1; 512/8; 512/25; 512/26; 512/27; 568/303; 568/379
(58) Field of Search ........................... 512/1, 25, 8, 26, 512/27; 568/303, 379

(56) References Cited

U.S. PATENT DOCUMENTS

| | | | | |
|---|---|---|---|---|
| 3,941,828 A | * | 3/1976 | Buchi | 560/122 |
| 4,217,251 A | * | 8/1980 | Dastur | 512/8 |
| 4,904,640 A | * | 2/1990 | Markert et al. | 512/8 |
| 4,990,496 A | | 2/1991 | Fehr et al. | 512/24 |
| 5,155,095 A | | 10/1992 | Blanc et al. | 512/21 |
| 5,760,277 A | * | 6/1998 | Naef et al. | 560/121 |
| 6,506,793 B2 | | 1/2003 | Tanaka et al. | 514/463 |

FOREIGN PATENT DOCUMENTS

| | | |
|---|---|---|
| CH | 580 555 | 10/1976 |
| JP | 56 128728 | 10/1981 |

OTHER PUBLICATIONS

Dr. Paul Dubs et al., "Synthesis of Three Jasmin Constituents via a Central Intermediate", Helvetica Chimica Acta, vol. 61, No. 87, pp. 990–997 (1978).

John E. McMurry et al., "A Mild Procedure for Transforming Nitro Groups into Carbonyls. Application to the Synthesis of cis–Jasmone", Journal of the American Chemical Society, vol. 93, No. 20, pp. 5309–5311 (Oct. 6, 1971).

L. Crombie et al., "Synthesis of cis—Jasmone and Other cis—Retthrones", Journal Chem. Soc., pp. 1024–1027 (1969).

Dr. M. Schlosser et al., "Trans–Selective Olefin Syntheses", Angew. Chem. International Edition, vol. 5, No. 1, pp. 126–127 (1966).

"Cyclenones. VI.$^1$ The RetroaldolAldol Route to cis—Jasmone and Related Compounds", Journal Org. Chem, vol. 39, No. 15, pp. 2317–2318 (1974).

Dubs Paul: "Synthesis of Three Jasmone Constituents . . . ", Helvetica Chimica Acta, vol. 61(3), No. 87, 1978, pp. 990–997.

McCurry Patrick: "Cyclenones . . . ", J Org Chem, vol. 39, No. 15, 1974, pp. 2317–2319.

Chemical Abstracts, vol. 98, No. 21, May 23, 1983, Abstract No. 179066, XP002245946.

Chemical Abstracts, vol. 98, No. 21, May 23, 1983, Abstract No. 179065, XP002245947.

Chemical Abstracts, vol. 96, No. 5, Feb. 1, 1982, Abstract No. 34688, XP002245948.

Chemical Abstracts, vol. 93, No. 5, Aug. 4, 1980, Abstract No. 46006, XP002245949.

* cited by examiner

Primary Examiner—Monique T. Cole
(74) Attorney, Agent, or Firm—Fitzpatrick, Cella, Harper & Scinto

(57) ABSTRACT

An excellent fragrance compound having high palatability. A 3-(3-hexenyl)-2-cyclopentenone represented by a general formula (1)

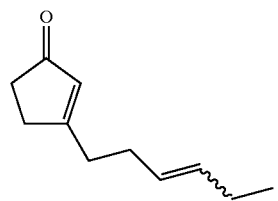

(wherein wavy line represents a double bond cis-form and/or trans-form) is used as an active ingredient of scent and mixed in a small amount with fragrance compositions, cis-jasmone and/or various materials to be scented. Since the above compound has a characteristic fragrance quality and high palatability, it is markedly useful as a scenting component of various fragrances and cosmetics, sanitation materials and the like.

5 Claims, No Drawings

FRAGRANCE COMPOSITION CONTAINING 3-(3-HEXENYL)-2-CYCLOPENTENONE

FIELD OF THE INVENTION

This invention relates to a fragrance composition which contains a 3-(3-hexenyl)-2-cyclopentenone represented by a general formula (1)

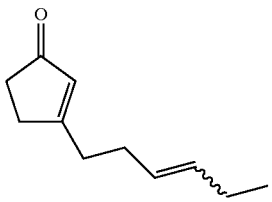

(wherein the wavy line represents a double bond for cis-form and/or trans-form) and a cis-jasmone. It also relates to a method for adding fragrance using the aforementioned compound.

BACKGROUND OF THE INVENTION

In recent years, with the diversification of various fragrances and cosmetics, sanitation materials and the like, formerly unknown new demand has been increasing for a fragrance to be used in their scenting (adding fragrance), with requirements that it must be a unique aroma having high palatability, be chemically stable and have excellent compounding ability with other fragrances to be used.

Accordingly, it is markedly important for the fragrance industry to develop a fragrance material which satisfies these requirements.

Up to date, a large number of fragrances have been identified from natural sources and reported; for example, cis-jasmone is frequently used as a high-class jasmine fragrance material because of its excellent fragrance quality.

3-(3Z-Hexenyl)-2-cyclopentenone (2(Z)) is known as a by-product formed during the synthesis of cis-jasmone (4) by, e.g., aldol condensation of 8Z-undecan-8-ene-2,5-dione (3) (*Helv. Chim. Acta.*, 61, 990 (1978), CH 580555 (1976)). Also, it has been reported as a material for synthesizing cis-jasmone by retro-aldol reaction (*J. Am. Chem. Soc.*, 93, 5309 (1971)).

However, 3-(3Z-hexenyl)-2-cyclopentenone (2(Z)) is a by-product unnecessary for the cis-jasmone synthesis and merely recognized as a simple reaction material, and it has not been known that it is markedly useful as a fragrance material. In addition, as for its double bond isomer 3-(3E-hexenyl)-2-cyclopentenone, we found no reports even on the compound itself.

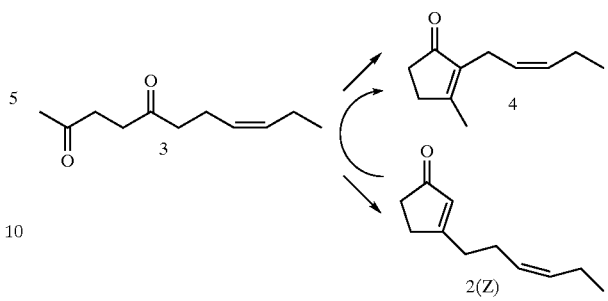

SUMMARY OF THE INVENTION

An object of the invention is to provide a highly palatable excellent fragrance compound which satisfies the aforementioned requirements. Also, it is to provide a fragrance composition which contains said fragrance compound as the active ingredient.

Also, during various studies on cis-jasmone, the present inventors have found unexpectedly that the aroma of cis-jasmone after removing impurities by a purification treatment (to be referred to as purification treated cis-jasmone hereinafter) has only a flat and low impact jasmine fragrance. In addition, it was found that a fragrance composition having markedly good fragrance quality can be obtained by blending the purification treated cis-jasmone with a specified compound.

Thus, an object of the present invention is to provide a cis-jasmone having high palatability and excellent fragrance quality, based on the aforementioned purification treated cis-jasmone.

As a result of intensive studies carried out with the aim of meeting the aforementioned requirements, the inventors found that a 3-(3-hexenyl)-2-cyclopentenone shown below has a unique aroma having high palatability and shows excellent harmony with other fragrance to be used, and that a cis-jasmone obtained by blending the purification treated cis-jasmone with a specified amount of the 3-(3-hexenyl)-2-cyclopentenone has the aroma of conventionally known cis-jasmone or more superior aroma than that, and finally have completed the present invention after further carrying out the studies.

Accordingly, the invention is to provide a fragrance composition and a cis-jasmone, characterized in that they contain a 3-(3-hexenyl)-2-cyclopentenone represented by a general formula (1)

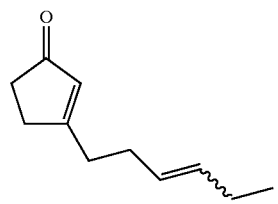

(wherein the wavy line represents a double bond for cis-form and/or trans-form).

DETAILED DESCRIPTION OF THE INVENTION

The following describes the invention in detail.

The 3-(3-hexenyl)-2-cyclopentenone of the present invention represented by the formula (1) means 3-(3E-hexenyl)-

2-cyclopentenone alone whose side chain is trans-form, 3-(3Z-hexenyl)-2-cyclopentenone alone whose side chain is cis-form or a mixture thereof.

These compounds or mixtures have excellent aroma and therefore are effective as fragrances. Particularly, the 3-(3Z-hexenyl)-2-cyclopentenone having cis-form side chain has excellent aroma and therefore is effective as a fragrance.

That is, each of the aforementioned compounds has green, floral, citrus, fatty and nitrile like characteristic aromas, and the trans-form has more strong greenness while the cis-form has more strong fruitiness.

In addition, by preparing a fragrance composition by mixing the 3-(3-hexenyl)-2-cyclopentenone as the compound of the invention with a generally used fragrance component, a voluminous, natural and impact body note can be added to the fragrance composition, so that it can be said that this is a considerably useful high-class fragrance which produces aroma having "texture".

The 3-(3E-hexenyl)-2-cyclopentenone of the invention represented by the formula (1) is a compound which has not been described in references yet. This compound can be produced, e.g., by the following method. That is, in the synthesis route of cis-jasmone by cis-selective Wittig reaction of furanyl aldehyde synthesized from 2-methylfuran and acrolein (*J. Chem. Soc.*, C, 1024 (1969)), corresponding trans-form is obtained by applying the trans-selective Wittig reaction conditions described in a reference (*Angew. Chem. Int. Ed. Engl.*, 5, 126 (1966)). By carrying out cyclization of this product through acidic hydrolysis and basic aldol condensation under similar conditions of the cis-form synthesis, a mixture of corresponding trans-jasmone and 3-(3E-hexenyl)-2-cyclopentenone is obtained. The 3-(3E-hexenyl)-2-cyclopentenone of interest can be separated and prepared by subsequent silica gel column chromatography separation.

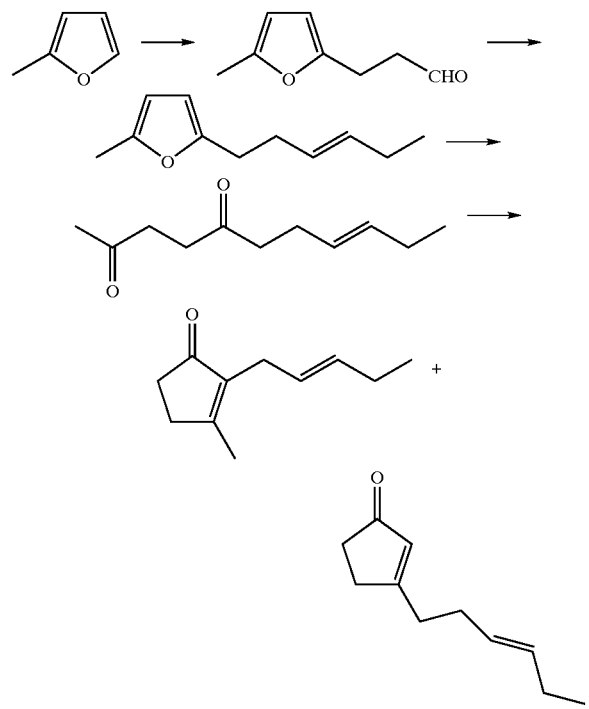

Also, though the production method of 3-(3Z-hexenyl)-2-cyclopentenone is not particularly limited, it can be obtained in an amount of several % as a by-product at the time of the aforementioned cis-jasmone synthesis and it can also be produced the following reported method. For example, a route for synthesizing it by 1,2-adding 3Z-hexenyl lithium to cyclopentenone and then oxidizing it via allyl rearrangement has been reported (*J. Org. Chem.*, 39, 2317 (1974)).

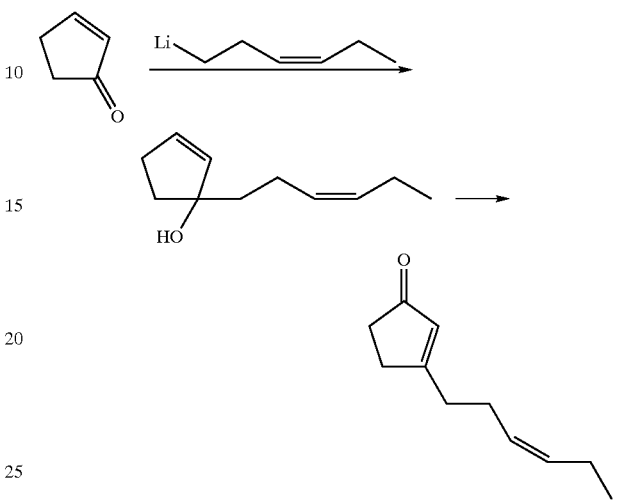

A mixture of 3-(3Z-hexenyl)-2-cyclopentenone (2(Z)) and 3-(3E-hexenyl)-2-cyclopentenone (2(E)) can be obtained by respectively preparing both of them and then mixing them at a optional mixing ratio.

The production method of purification treated cis-jasmone is described below. The production method of purification treated cis-jasmone is not particularly limited. That is, it can be easily prepared by treating a reaction product obtained employing a known cis-jasmone production method and employing a known purification method in the conventional way. As a typical production method of cis-jasmone, the aforementioned synthesis route of cis-jasmone in which cis-selective Wittg reaction of furanyl aldehyde synthesized from 2-methylfuran and acrolein is carried out and then cyclization of the product is carried out by acidic hydrolysis and basic aldol condensation can be exemplified (*J. Chem. Soc.*, C, 1024 (1969)). The purification treated cis-jasmone can be obtained by subjecting the cis-jasmone obtained by this route to a separation purification treatment, e.g., by a silica gel column chromatography using a hexane-ethyl acetate mixed solvent.

When the thus obtained purification treated cis-jasmone having inferior fragrance quality is blended with the aforementioned 3-(3-hexenyl)-2-cyclopentenone, the cis-jasmone having excellent fragrance quality as described in the invention can be obtained. It is desirable that the blending amount of the aforementioned 3-(3-hexenyl)-2-cyclopentenone with the purification treated cis-jasmone is adjusted to a level of from 0.01 to 0.5% by weight based on the purification treated cis-jasmone. From the viewpoint of obtaining a cis-jasmone having palatability, it is desirable that said blending amount is adjusted to a level of from 0.02 to 0.3% by weight, more desirably from 0.05 to 0.15% by weight.

Method for producing the cis-jasmone of the invention having excellent fragrance quality is not limited to the aforementioned method. That is, it may be prepared by a distillation process, a column chromatography purification or the like any method, with the proviso that the aforementioned 3-(3-hexenyl)-2-cyclopentenone is present in cis-jasmone in the aforementioned blending amount as a result.

Since the 3-(3-hexenyl)-2-cyclopentenone and/or cis-jasmone having excellent fragrance quality of the invention can produce desirable aroma even when added in a extremely small amount, it becomes possible to add fragrance to base materials of various fragrances and cosmetics which require scenting of fragrance. That is, though it varies depending on each material to be scented, excellent effect can be exerted, e.g., by blending 3-(3-hexenyl)-2-cyclopentenone in an amount of approximately 0.0000001% by weight based on the material to be scented.

In this connection, since 3-(3-hexenyl)-2-cyclopentenone has a characteristic fragrance and excellent long-lasting property, it may be used alone as a fragrance component, and it can also be used as a fragrance composition by mixing one or two of its double bond isomers with a generally used fragrance component.

The term "fragrance composition" as used herein means a mixture of 3-(3-hexenyl)-2-cyclopentenone and/or cis-jasmone having excellent fragrance quality with one or two or more of generally used fragrance components. As the generally used fragrance components as used herein, a broad range of fragrances can be used with no particular limitation, e.g., the components described by Arctander S., in "Perfume and Flavor Chemicals", published by the author, Montolair, N.J. (U.S.A.), 1969, can be used. The typical examples include α-pinene, limonene, menthol, phenylethyl alcohol, styrallyl acetate, eugenol, rose oxide, linalool, benzaldehyde, muscone, methyl dihydrojasmonate, cis-jasmone, dihydrojasmone, γ-undecalactone, hexylcinnamic aldehyde, jasmal, heliobouquet and the like, though not particularly limited thereto.

The blending amount of the 3-(3-hexenyl)-2-cyclopentenone of the present invention in the fragrance composition varies depending on the kind and purpose of the formulating fragrance, but it is desirable to use the compound in an amount of from about 0.000001% by weight to 10% by weight, preferably from about 0.00001% by weight to 1% by weight, more preferably from about 0.0001% by weight to 0.1% by weight, in the composition.

Also, the blending amount of the cis-jasmone of the present invention in the aforementioned fragrance varies depending on the kind and purpose of the formulating fragrance, but it is desirable to use the compound in an amount of from 0.001 to 20% by weight, particularly from 0.01 to 10% by weight in the composition.

When the 3-(3-hexenyl)-2-cyclopentenone and/or cis-jasmone having excellent fragrance quantity of the invention alone or a fragrance composition containing said component is added to fragrance-containing products such as shampoo, rinses and the like fragrance, its diffusing ability and suspending ability can be increased and a fresh and highly palatable aroma can be added.

The fragrance or fragrance composition of the present 1invention can be used suitably as a fragrance component in fragrances and cosmetics, sanitation materials, medicaments and the like. That is, when it is used in shampoo, rinses, a perfume, colognes, hair tonics, hair creams, pomades, hair cosmetic base materials, other cosmetic base materials, cosmetic cleansers, interior aromatics, soaps, dish washing detergents, washing detergents, softening agents, disinfection detergents, deodorization detergents, a furniture care, disinfectants, germicides, repellents, bleachers, other various sanitation detergents, dentifrice, mouse washes, toilet papers, excipients for improving taking of medicaments and the like, their market values can be increased.

The present invention is described in the following by Examples and Comparative Examples, but the present invention is not limited thereto. In this connection, measuring instruments and measuring conditions used in the examples are shown below.

(1) Gas chromatography (GC);
   Instrument: HP-6890A (mfd. by Hewlett-Packard Company)
   Column: HP-5 (30 m×0.32 mm×0.25 μm) (mfd. by Hewlett-Packard Company)
   Carrier Gas: Helium
   Measuring temperature: 100 to 220° C. (temperature rising at 10° C./min)
(2) Infrared absorption spectrum (IR);
   Instrument: AVATAR 360 FT-IR (mfd. by Thermo Nicolet Japan Inc.)
(3) Proton nuclear magnetic resonance spectrum ($^1$H-NMR);
   Instrument: DRX-500 (500 MHz) (mfd. by Brucker)
   Internal standard substance: tetramethylsilane
(4) Mass spectrum (MS);
   Instrument: M-80B mass spectrometer (ionization voltage: 20 eV) (mfd. by Hitachi Ltd.)

EXAMPLE 1a

Synthesis of 2-(3E-hexenyl)-5-methylfuran

A 2,000 ml capacity four neck reactor equipped with a thermometer and a condenser was charged with n-propyltriphenylphosphonium bromide (0.141 mol) and anhydrous tetrahydrofuran (THF) (300 ml). Under stirring at −60° C., phenyllithium diethyl ether solution (0.50 mol/l, 261 ml) was added dropwise thereto spending 1 hour. By removing the cold bath, the temperature was increased to 0° C. spending 1.5 hours and then stirred as such for 1 hour. To this was added dropwise anhydrous ethyl ether solution (100 ml) containing 15 0 g (0.109 mol) of 3-(5-methylfuran-2-yl)propanal at −70° C. spending 1.5 hours. Then, by removing the cold bath, the temperature was increased to −30° C. spending 40 minutes. Thereafter, phenyllithium ethyl ether solution (0.50 mol/l, 368 ml) was again added dropwise thereto spending 1 hour and stirred for 15 minutes, and then a hydrogen chloride ethyl ether solution (5.6 mol/l, 114 ml) was added dropwise thereto at −30° C. spending 45 minutes, followed by stirring as such for 5 minutes. Finally, potassium t-butoxide (92.4 g, 0.823 mol) was added dropwise thereto at −30° C. spending 10 minutes, and then anhydrous diethyl ether (600 ml) was added thereto and, after removing the cold bath, the contents were stirred for 2.5 hours. The reaction was stopped by pouring the reaction solution into water, and the organic layer was washed with water and saturated brine, dried with anhydrous sodium sulfate and then concentrated under a reduced pressure. This concentrate was washed with pentane and the dissolved oil fraction was concentrated to obtain 24.3 g of crude product which was then subjected to simple distillation to obtain 13.4 g (yield 74%, bp 78° C./120 Pa) of 2-(3E-hexenyl)-5-methylfuran (cis/trans=7/93).

$^1$H-NMR (500 MHz, CDCl$_3$, δ) ppm: 0.96 (t, 3 H, J=7.5 Hz), 1.95–2.04 (m, 2 H), 2.25 (s, 3 H), 2.27–2.34 (m, 2 H), 2.58–2.64 (m, 2 H), 5.38–5.54 (m, 2 H), 5.82–5.86 (m, 2 H).

IR (film) cm$^{-1}$: 2961, 1570, 1219, 1022, 966.

MS (m/e): 164 (M+), 133, 121, 108, 95, 91, 77, 67, 65, 53, 43, 41, 39, 27.

EXAMPLE 1b

Synthesis of 8E-undecene-2,5-dione

A 100 ml capacity four neck flask equipped with a thermometer and a condenser was charged with 2-(3E- hexenyl)-5-methylfuran (8.65 g, 52.7 mmol), acetic acid (8.99 g), water (4.47 g) and concentrated sulfuric acid (0.12 g), followed by stirring at 97° C. for 3 hours. Hexane and water were added to the reaction solution to effect separation of layers, and the organic layer was washed with water twice and with saturated brine, dried with anhydrous sodium sulfate and then concentrated under a reduced pressure to obtain 9.51 g of crude product. By separating and purifying this product by a silica gel column chromatography (hexane/ethyl acetate=15/1 (volume ratio)), 8.38 g of 8E-undecene-2,5-dione was obtained (yield 88%, cis/trans=7/93 (weight ratio)).

$^1$H-NMR (500 MHz, CDCl$_3$, δ) ppm: 0.95 (t, 3 H, J=7.5 Hz), 1.94–2.02 (m, 2 H), 2.22–2.30 (m, 2 H), 2.48–2.55 (m, 2 H), 2.64–2.73 (m, 4 H), 5.32–5.40 (m, 1 H), 5.44–5.52 (m, 1 H).

IR (film) cm$^{-1}$: 3028, 2963, 2933, 1713, 1403, 1367, 1173, 1096, 969.

MS (m/e): 182 (M+), 124, 114, 99, 95, 83, 71, 69, 55, 43, 41, 29.

EXAMPLE 1c

Synthesis of 3-(3E-hexenyl)-2-cyclopentenone

A 100 ml capacity four neck flask equipped with a thermometer and a condenser was charged with 8E-undecene-2,5-dione (7.0 g, 38.4 mmol), 50% sodium hydroxide (2.31 g) and water (28.2 g), followed by stirring at 97° C. for 5 hours. Hexane and water were added to the reaction solution to effect separation of layers, and the organic layer was washed with water twice and with saturated brine, dried with anhydrous sodium sulfate and then concentrated under a reduced pressure to obtain 6.1 g of crude product. By separating and purifying this product by a silica gel column chromatography (hexane/ethyl acetate=10/1 (volume ratio)), 0.35 g of 3-(3E-hexenyl)-2-cyclopentenone was obtained (yield 6%, cis/trans=7/93 (weight ratio)).

$^1$H-NMR (500 MHz, CDCl$_3$, δ) ppm: 0.96 (t, 3 H, J=7.5 Hz), 1.96–2.04 (m, 2 H), 2.24–2.32 (m, 2 H), 2.36–2.42 (m, 2 H), 2.44–2.5 (m, 2 H), 2.55–2.60 (m, 2 H), 5.33–5.42 (m, 1 H), 5.47–5.56 (m, 1 H), 5.96 (br. s, 1 H).

IR (film) cm$^{-1}$: 3028, 2962, 2926, 1712, 1675, 1616, 1438, 1185, 970.

MS (m/e): 164 (M+), 149, 136, 122, 107, 96, 91, 79, 69, 53, 41, 39, 27.

EXAMPLE 2

Preparation of Purification Treated cis-jasmone and 3-(3Z-hexenyl)-2-cyclopentenone Using 8Z-undecene-2,5-dione (7.0 g) obtained in accordance with the aforementioned reference (*J. Org. Chem.*, 31, 977 (1966)) instead of the 8E-undecene-2,5-dione of Example 1c, crude cis-jasmone was synthesized in the same manner and then separated and purified by a silica gel column chromatography (hexane/ethyl acetate=10/1) to obtain purification treated cis-jasmone (5.5 g, yield 87%) and 3-(3Z-hexenyl)-2-cyclopentenone (0.33 g, yield 5%).

3-(3Z-hexenyl)-2-cyclopentenone $^1$H-NMR (500 MHz, CDCl$_3$, δ) ppm: 0.96 (t, 3 H, J=7.5 Hz), 2.01–2.09 (m, 2 H), 2.30–2.38 (m, 2 H), 2.36–2.42 (m, 2 H), 2.44–2.5 (m, 2 H), 2.55–2.60 (m, 2 H), 5.27–5.34 (m, 1 H), 5.40–5.48 (m, 1 H), 5.96 (br. s, 1 H).

IR (film) cm$^{-1}$: 3007, 2962, 2932, 1712, 1675, 1616, 1438, 1185.

MS (m/e): 164 (M+), 149, 136, 122, 107, 96, 91, 79, 69, 53, 41, 39, 27.

EXAMPLE 3

Evaluation of Fragrance Quality

Odor evaluation of the 3-(3-hexenyl)-2-cyclopentenone synthesized in Example 1 and Example 2 was carried out by a panel of seven professional analysts.

The results are shown in Table 1.

TABLE 1

| Compound name | Odor evaluation (fragrance evaluation) |
|---|---|
| 3-(3-Hexenyl)-2-cyclopentenone (Z/E = 1/1 (weight ratio) | Green, floral, citrus, fatty and nitrile-like |
| 3-(3Z-Hexenyl)-2-cyclopentenone | More fatty fruity, floral and nitrile-like |
| 3-(3E-Hexenyl)-2-cyclopentenone | More green floral and nitrile-like |

Thus, the compound of the invention was possessed of green, floral, citrus and nitrile-like characteristic aromas having high palatability.

EXAMPLE 4

Evaluation of Fragrance Quality

The 3-(3Z-hexenyl)-2-cyclopentenone obtained in Example 2 was added to the purification treated cis-jasmone obtained in Example 2 in the varied amounts shown in Table 2, and sensory test on the changes in aroma and palatability of the thus obtained cis-jasmone samples was carried out by a panel of seven professional analysts.

The results are shown in Table 2.

TABLE 2

| Samples | Added amount (weight %) | Comparative sensory evaluation |
|---|---|---|
| Purification treated cis-jasmone (control) | 0 | X |
| Added sample-1 | 0.01 | ○ |
| Added sample-2 | 0.05 | ○○ |
| Added sample-3 | 0.08 | ○○ |
| Added sample-4 | 0.1 | ○○ |
| Added sample-5 | 0.15 | ○○ |
| Added sample-6 | 0.5 | ○ |
| Added sample-7 | 1.0 | X |

○○: Palatability of cis-jasmone aroma was markedly improved.
○: Palatability of cis-jasmone aroma was improved.
X: Palatability of cis-jasmone aroma was reduced.

As shown in the above, it was confirmed that addition of the 3-(3-hexenyl)-2-cyclopentenone having very strong characteristic aroma greatly exerts influences on the cis-jasmone aroma. That is, in the samples prepared by adding appropriate amounts of 3-(3-hexenyl)-2-cyclopentenone to the purification treated cis-jasmone, an impact, green floral natural texture was clearly improved, and the palatability provided with a voluminous feeling and a high-class feeling was clearly improved compared to the non-addition sample. However, its effective concentration was limited, which was within a narrow range of from 0.01 to 0.5% by weight based on the purification treated cis-jasmone. The concentration smaller than that showed no particular addition effects, and larger than that resulted in too strong fatty and nitrile-like greenness originated from the 3-(3-hexenyl)-2-cyclopentenone, and on the contrary, palatability as the cis-jasmone aroma was reduced.

EXAMPLE 4

Production of Fragrance Composition for Shampoo Use

| Formulation example | (Weight) |
|---|---|
| Aldehyde C14 (10% DPG) | 30 |
| Allyl cyclohexylpropionate | 5 |
| Ambroxan (10% DPG) | 10 |
| Benzyl acetate | 120 |
| Dimethylbenzylcarbinyl acetate | 10 |
| Methyl dihydrojasmonate | 140 |
| Heliobouquet | 15 |
| Cis-3-hexenol | 5 |
| Hexylcinnamic aldehyde | 60 |
| Indole (10% DPG) | 10 |
| Cis-jasmone | 5 |
| Kovanol | 25 |
| Lilial | 120 |
| Linalool | 150 |
| Linaryl acetate | 40 |
| Methylchabicol (10% DPG) | 10 |
| Ethylene brassylate | 80 |
| Nopil acetate | 30 |
| Oak moss No. 1 | 5 |
| Rasberry ketone (10% DPG) | 35 |
| Fruit base | 40 |
| Tonalid | 40 |
| Subtotal | 985 |
| 3-(3Z-Hexenyl)-2-cyclopentenone (1% DPG) | 15 |
| Total | 1000 |

Comparative Example 1

A fragrance composition for shampoo use was prepared by the same formulation of Example 3, except that dipropylene glycol (DPG) was used instead of 3-(3Z-hexenyl)-2-cyclopentenone (1% DPG) in the formulation of Example 4.

Evaluation result of Example 4 and Comparative Example 1

As a result of the evaluation of the fragrance compositions of Example 4 and Comparative Example 1, it was able to add a voluminous green floral body note to the fragrance composition containing 3-(3Z-hexenyl)-2-cyclopentenone based on the formulation of Example 4.

EXAMPLE 5

Production of Fragrance Composition for Soap Use

| Formulation example | (Weight) |
|---|---|
| Aldehyde C11 | 3 |
| Benzyl acetate | 45 |
| Bergamot oil | 120 |

-continued

| Formulation example | (Weight) |
|---|---|
| Celery seed oil | 5 |
| Civet oil (10% DPG) | 5 |
| Coumarin | 2.5 |
| Galaxolide 50BB | 75 |
| Hexylcinnamic aldehyde | 185 |
| Isobutylquinoline (1% DPG) | 3 |
| Iso E super | 50 |
| Jasmine absolute (10% DPG) | 5 |
| Cis-jasmone | 5 |
| Kovanol | 75 |
| Lemon oil guinea | 120 |
| Mandarin red oil | 40 |
| Methyl ionone gamma | 180 |
| Meal oil | 1.5 |
| Nutmeg oil | 5 |
| Oak moss No. 1 | 5 |
| Patchouli oil | 40 |
| Rosemary oil | 10 |
| Violet leaf absolute (10% DPG) | 5 |
| Ylang oil | 5 |
| Subtotal | 990 |
| 3-(3E-Hexenyl)-2-cyclopentenone (1% DPG) | 10 |
| Total | 1000 |

Comparative Example 2

A fragrance composition for soap use was prepared by the same formulation of Example 5, except that dipropylene glycol (DPG) was used instead of 3-(3E-hexenyl)-2-cyclopentenone (1% DPG) in the formulation of Example 5.

Evaluation Result of Example 5 and Comparative Example 2

As a result of the evaluation of the fragrance compositions of Example 5 and Comparative Example 2, it was able to add impact of a green floral-like natural body note to the fragrance composition containing 3-(3E-hexenyl)-2-cyclopentenone based on the formulation of Example 5.

EXAMPLE 6

Production of Fragrance Composition for Perfume Use

| Formulation example | (Weight) |
|---|---|
| Alfa terpineol | 5 |
| Ambroxan | 2 |
| Cassis base | 2 |
| L-Citronellol | 30 |
| Cyclogalbanate | 3 |
| Cypress oil | 2 |
| Damascone alpha (10% DPG) | 5 |
| DPG | 2 |
| Ethyl acetoacetate | 35 |
| Ethyl linalool | 35 |
| Cyclopentadecanolide | 45 |
| Florosa 80 DPG | 10 |
| Galaxolide 50 BB | 200 |
| Galbanum oil | 1 |
| Methyl dihydrojasmonate | 250 |
| Heliobouquet | 30 |
| Hexylcinnamic aldehyde | 20 |
| Iso E super | 25 |
| Jasmine absolute (10% DPG) | 5 |
| Kovanol | 30 |

-continued

| Formulation example | (Weight) |
| --- | --- |
| Lilial | 70 |
| Methyl ionone gamma | 20 |
| Methylphenyl acetate (10% DPG) | 3 |
| Ethylene brassylate | 80 |
| Patchouli oil | 1 |
| Phenylethyl alcohol | 15 |
| Rose absolute | 2 |
| Rose oil | 5 |
| Rosephenone | 1 |
| Styrallyl acetate | 1 |
| Tripral | 3 |
| Ylang oil | 2 |
| 3-(3-Hexenyl)-2-cyclopentenone (1% DPG) | 60 |
| Total | 1000 |

Comparative Example 3

A fragrance composition for perfume use was prepared by the same formulation of Example 6, except that dipropylene glycol (DPG) was used instead of 3-(3-hexenyl)-2-cyclopentenone (1% DPG) in the formulation of Example 6.

Evaluation Result of Example 6 and Comparative Example 3

As a result of the evaluation of the fragrance compositions of Example 6 and Comparative Example 3, it was able to add a green floral, refreshing and natural impact to the fragrance composition containing 3-(3-hexenyl)-2-cyclopentenone based on the formulation of Example 6.

The 3-(3-hexenyl)-2-cyclopentenone and cis-jasmone provided by the invention have characteristics in that they can produce a desirable aroma by their addition in small amounts and also can produce an aroma having so-called "body" and "depth". In other words, it can be said that the aforementioned 3-(3-hexenyl)-2-cyclopentenone and cis-jasmone are high-class fragrances which produce an aroma having so-called "texture". What is more, they are markedly important fragrances as a component of compound fragrances because they have excellent compatibility with other fragrances and many compounds, so that it was able to make a possibility to add fragrances to various aromatic cosmetics, sanitation materials and the like base materials which require scenting of fragrances.

While the invention has been described in detail and with reference to specific embodiments thereof, it will be apparent to one skilled in the art that various changes and modifications can be made therein without departing from the scope thereof.

This application is based on Japanese patent applications No. 2001-385182 filed Dec. 18, 2001 and No. 2001-385183 filed Dec. 18, 2001, the entire contents thereof being hereby incorporated by reference.

What is claimed is:

1. A fragrance composition comprising a 3-(3-hexenyl)-2-cyclopentenone represented by

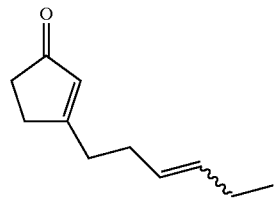

(wherein the wavy line represents cis-form and/or trans-form).

2. A method for adding fragrance, comprising blending a 3-(3-hexenyl)-2-cyclopentenone represented by

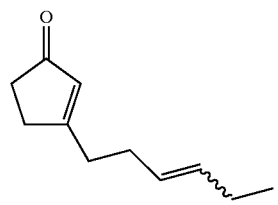

(wherein the wavy line represents cis-form and/or trans-form) with a material to be scented.

3. A cis-jasmone comprising a 3-(3-hexenyl)-2-cyclopentenone represented by

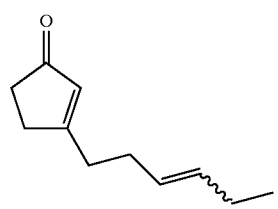

(wherein the wavy line represents cis-form and/or trans-form).

4. The cis-jasmone according to claim 3, comprising from 0.01 to 0.50% by weight of the 3-(3Z-hexenyl)-2-cyclopentenone.

5. A 3-(3E-hexenyl)-2-cyclopentenone represented by

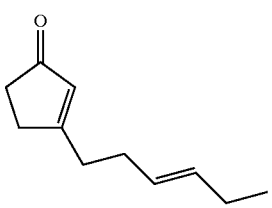

* * * * *